United States Patent [19]

Huth

[11] Patent Number: 5,079,356

[45] Date of Patent: Jan. 7, 1992

[54] ETHYLENICALLY UNSATURATED UREA DERIVATIVES

[75] Inventor: Hans-Ullrich Huth, Egelsbach, Fed. Rep. of Germany

[73] Assignee: Hoechst AG, Fed. Rep. of Germany

[21] Appl. No.: 547,793

[22] Filed: Jul. 2, 1990

Related U.S. Application Data

[62] Division of Ser. No. 354,129, May 19, 1989.

[30] Foreign Application Priority Data

May 21, 1988 [DE] Fed. Rep. of Germany ....... 3817468

[51] Int. Cl.$^5$ ............................................. C07D 401/06
[52] U.S. Cl. .................................... 540/524; 544/129;
544/141; 544/162; 546/189; 546/208; 546/245;
548/538
[58] Field of Search ........................ 546/245, 189, 208;
544/129, 141, 162; 540/524; 548/538

[56] References Cited

U.S. PATENT DOCUMENTS 4,912,127 3/1990 Henning et al. ..................... 514/422

Primary Examiner—Joseph Paul Brust
Assistant Examiner—Jacqueline Haley
Attorney, Agent, or Firm—Bierman and Muserlian

[57] ABSTRACT

Urea derivatives with $\alpha,\beta$-ethylenically unsaturated carboxyl or carboxamide radicals, produced by reaction of ethylenically unsaturated isocyanates with ammonia or amines or by reaction of ethylenically unsaturated amines with isocyanates in the absence of water, optionally in bulk, it being possible to carry out the reaction for improved reaction control advantageously in inert organic solvents or also in so-called reactive diluents, i.e. copolymerizable ethylenically unsaturated monomeric compounds which remain inert under the reaction conditions, such as for example vinyl esters, (meth-)acrylates, vinyl aromatics.

The urea derivatives produced according to the invention have in their monomeric form slight to moderate or in some cases good solubility in water and/or in organic solvents. They are polymerizable or copolymerizable via their $\alpha, \beta$-ethylenically unsaturated carboxyl or carboxamide groups and can be multiferiously used by free-radical initiated polymerization or copolymerization for the production of polymers or copolymers.

5 Claims, No Drawings

ETHYLENICALLY UNSATURATED UREA DERIVATIVES

PRIOR APPLICATION

This application is a division of U.S. patent application Ser. No. 354,129 filed May 19, 1989 pending.

The invention relates to ethylenically unsaturated urea derivatives particularly urea derivatives with (meth)-acrylate groups or (meth)acrylamide groups, some of which have valuable solubilities in water and/or organic solvents and among other attributes can be free-radical polymerized or copolymerized, and to a process for their preparation.

Ethylenically unsaturated urea derivatives with (meth)-allyl groups and their use as comonomers in emulsion polymerization have already been disclosed in European Patent 3870. When used as monomers however they exhibit the disadvantages known in allyl polymerization.

EP-OS 197,635 discloses ethylenically unsaturated urea compounds having (meth)acrylate radicals, whose urea group is substituted at the nitrogen atom adjacent to the (meth)acrylate group by hydrogen and at the other nitrogen atom by a relatively large organic radical having at least 5 carbon atoms. These urea compounds do not exhibit significant solubilities either in water or in most organic solvents. They can be used for the production of low viscosity thickener dispersions by copolymerization with $\alpha,\beta$-ethylenically unsaturated carboxylic acids and other comonomers, these dispersions being convertible into highly viscous aqueous solutions by adjustment of their pH to about 9. These products are said to have an improved resistance to hydrolysis and improved resistances to electrolytes, in comparison with other conventional thickeners, and can be used for improving the rheological properties of aqueous systems. No information is given concerning other uses of these products.

Surprisingly, urea derivatives with $\alpha, \beta$-ethylenically unsaturated carboxyl radicals or carboxamide radicals have now been found, which have slight or moderate to good solubilities in water and/or in organic solvents, are polymerizable and copolymerizable and can be advantageously and multifariously used, for example for the production of polymers or copolymers.

The invention therefore relates to ethylenically unsaturated urea derivatives of the formula I,

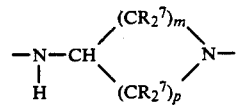

in which the radicals $R^1$ to $R^5$ and Z signify the following:

$R^1$, $R^2$, $R^3$, which may be identical or different, =H or $CH_3$,

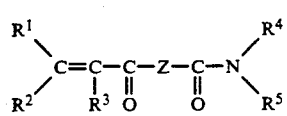

Y=oxygen or NH, n=2 to 4, preferably 2,
$R^6$=an optionally substituted $(C_1-C_4)$-alkyl, $R^7$=H or $CH_3$ and m, p=in each case at least the number 1, preferably $m+p=3$ to 5, $R^4$, $R^5$, which may be identical or different, =H, an optionally substituted $(C_1-C_{30})$-alkyl, preferably $(C_1-C_{18})$-alkyl, an optionally substituted —$(C_kH_{2-k})$—OH with k=1 to 8, preferably 2 to 4, an optionally substituted $(C_6-C_{10})$-aryl, an optionally substituted $(C_7-C_{30})$-aralkyl, an optionally substituted $(C_5-C_8)$-cycloalkyl, an optionally substituted 5- to 7-membered heterocycle or an optionally substituted heterocycle formed from $R^4$ and $R^5$ together with the nitrogen atom.

Preferably $R^4$ stands for H, when Z denotes the radical

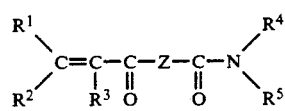

and $R^5$ denotes an optionally substituted 5- to 7-membered heterocycle, an optionally substituted $(C_5-C_8)$-cycloalkyl radical or an optionally substituted aryl radical, or when Z denotes the radical

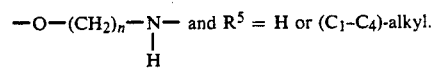 and $R^5$ = H or $(C_1-C_4)$-alkyl.

Preferred urea derivatives are moreover those in which, in the formula I, $R^1$, $R^2$=H and $R^3=CH_3$, or $R^1$, $R^2$=H, $R^3=CH_3$ and

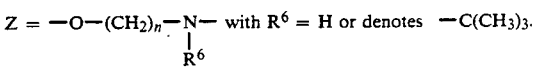

The invention furthermore relates to a process for the production of ethylenically unsaturated urea derivatives of the formula I

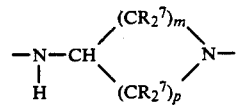 (I)

in which $R^1$ to $R^5$ and Z have the meanings previously mentioned, by reaction of isocyanates with ammonia or amines, which comprises a) reacting isocyanates of the formula II,

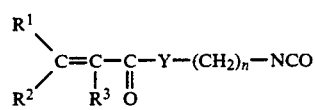 (II)

in which $R^1$, $R^2$, $R^3$, Y and n have the meaning as in formula I, with ammonia or primary or secondary amines of the formula III,

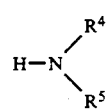 (III)

in which $R^4$ and $R^5$ have the meaning as in formula I and in the case of primary amines $R^4$ stands for H, or b) reacting amines of the formulae IV or V,

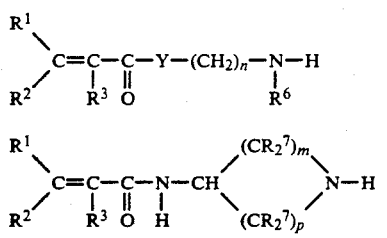

in which $R^1$, $R^2$, $R^3$, $R^6$, $R^7$, Y, n, m and p have the meaning as in formula I, with isocyanates of the formula VI, $$OCN-R^5 \quad (VI)$$

in which $R^5$ has the meaning as in formula I other than H.

The reaction is carried out according to the invention preferably in such a way that the reactions defined by a) and/or b) are carried out in bulk or preferably in inert organic solvents or in copolymerizable ethylenically unsaturated monomers which remain inert under the reaction conditions (reactive diluents) in the absence of water, preferably at temperatures between 0° C. and room temperature, or at a higher temperature, preferably up to 60° C.

The inert solvents conventionally used in organic syntheses with isocyanates in a dry medium are used as inert organic solvents, insofar as they fulfill among other requirements those regarding dissolving power and boiling range.

Preferred inert solvents are for example toluene, tetrahydrofuran (THF), ethyl acetate and hexane.

Moreover, so-called reactive diluents are preferred, i.e. copolymerizable monomers which remain inert under the synthesis conditions of the urea group formation according to the invention, but can subsequently be copolymerized under suitable polymerization conditions with the unsaturated urea derivatives of formula I according to the invention. Preferred inert reactive diluents are accordingly for example (meth)acrylates, styrene and vinyl esters, it being preferably to operate below the saturation concentration of the reactants when they are used.

A catalyst may optionally be co-used in the isocyanate addition according to the invention, among other reasons in order to be able to keep the reaction temperature as low as possible, which can be particularly advantageous when using reactive diluents. Preferred catalysts are organotin compounds, which are preferably used dissolved in an inert organic solvent. The use of dibutyltin dilaurate is particularly preferred.

Isocyanates which are preferably used as isocyanates of the formula II are those in which in formula II $R^1$ and $R^2$ stand for H or $CH_3$, preferably H, $R^3$ stands for H or $CH_3$, preferably $CH_3$, Y stands for O and n stands for 2 to 4, preferably 2.

As amine components of the formula III, ammonia, ($C_1$-$C_4$)-mono- or -dialkylamines, heterocyclic compounds having 5- to 7-membered rings such as pyrrole, pyrrolidine, piperidine or morpholine are preferably used.

Amines which are preferably used as amines of the formula IV are those in which in formula IV $R^1$, $R^2$, $R^3$=H or $CH_3$, preferably $R^1$, $R^2$=H and $R^3$=$CH_3$, Y=O, n=2 to 4, preferably 2, $R^6$=H or ($C_1$-$C_4$)-alkyl, preferably ($C_1$-$C_4$)-alkyl, particularly butyl, particularly preferably tert.-butyl.

Amines which are preferably used as amines of the formula V are those in which in formula V $R^1$, $R^2$, $R^3$ have the meaning as in formula IV, $R^7$=H or $CH_3$ and m+p=3 to 5, preferably m=2 and p=2, corresponding to a piperidine radical. Particularly preferred compounds of the formula V are those in which at least one radical $R^7$, particularly four radicals $R^7$, preferably four radicals $R^7$ in position 2 and position 6 of the heterocycle, denote $CH_3$.

The conventional known alkyl, aryl, aralkyl and cycloalkyl monoisocyanates in particular can be used as isocyanates of the formula VI. Particularly preferred are for example methyl isocyanate, ethyl isocyanate, butyl isocyanate, nonyl isocyanate, octadecyl isocyanate, phenyl isocyanate, 3-chlorophenyl isocyanate, 3-toluyl isocyanate and cyclohexyl isocyanate.

The compounds of the formula I produced according to the invention are in most cases obtained directly in crystalline form and can, optionally after removal of the co-used solvents under suction, be generally further used without further purification and drying as intermediate products. In some cases compounds of the formula I also occur in viscous-liquid form and can also be further used directly as intermediate products. Obviously, the crude reaction products produced in synthetic processes according to the invention can also be purified by conventional methods, such as for example elution, recrystallization, repreciptation and/or removal of volatile components by distillation optionally under reduced pressure, and the compounds of formula I produced in chemically pure form.

Solubility experiments have revealed, among other information, mation, that the solubilities of compounds of the formula I having $R^1$, $R^2$=H,

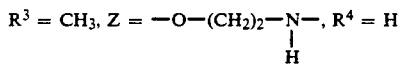

and $R^5$=H or ($C_1$-$C_4$)-alkyl exhibit a strong dependence on the type of radical $R^5$. Thus in the case of compounds in which $R^5$=H or $CH_3$, the solubility in water is surprisingly high (>10% by weight) and the compound having $R^5$=$CH_3$ moreover has good solubility in inert organic solvents and in inert reactive diluents. The solubility of the compounds both in water and in inert organic solvents decreases sharply with increasing size of the radical $R^5$ from ($C_2$)-alkyl up to ($C_4$)-alkyl.

This greatly variable solubility behavior opens up valuable possibilities for the use of urea derivatives of the formula I, particularly as comonomers in polymerizations. In this regard, it has surprisingly been found that dispersion polymers produced preferably by free-radical initiated emulsion or suspension polymerization and based on ethylenically unsaturated monomers and which contain at least 1% by weight of monomer units of the urea derivatives of the formula I of the present invention, have unexpectedly advantageous properties. These polymers or copolymers, their applicability, particularly in the form of their aqueous dispersions, and their production using monomeric urea derivatives of the formula I of the present invention as starting products are the subject-matter of the patent application HOE 88/F 124 (Az. P 38 17 469.3) filed on the same day, to which reference is hereby made.

The invention is described in more detail by the following examples.

EXAMPLE 1

Preparation of the Formula I Compound

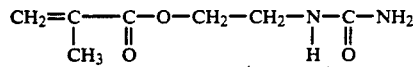

1.2 liters of dry n-hexane, 155.1 g (1 mol) of isocyanatoethyl methacrylate and 0.1 ml of dibutyltin dilaurate are placed in a four-necked flask with stirrer, thermometer, gas inlet pipe and reflux condenser with a $CaCl_2$ terminal pipe. Subsequently at least 1 mol of $NH_3$ as dry ammonia gas is passed with stirring into the reaction mixture directly below the surface of the liquid at a temperature of between 0° and 5° C. After a certain reaction time, the reaction mixture turns cloudy and the desired ethylenically unsaturated urea compound of the above-mentioned formula I begins to crystallize out. After a reaction time of about 2.5 hours, the reaction product is removed from the liquid component by suction filtration, washed three times with 100 ml of n-hexane and dried under vacuum. The yield of crystalline reaction product of the abovementioned formula I is 83.1 g (48.3% of theoretical yield), its melting point is 74°–77° C. The product is readily soluble in water and has good solubility in some organic solvents, such as for example toluene, acrylates, styrene. The IR spectrum and the $^1H$ NMR spectrum are consistent with the structure of the urea compound of the abovementioned formula I.

EXAMPLE 2

Preparation of the Formula I Compound

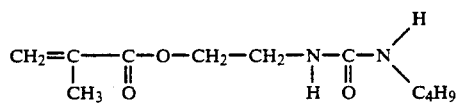

The apparatus described in Example 1 is used with the difference that the gas inlet pipe is replaced with a dropping funnel. 36.6 g (0.5 mol) of n-butylamine and 1 drop of dibutyltin dilaurate (Sn catalyst), dissolved in 100 ml of toluene, are placed in the flask and at room temperature with stirring 77.5 g (0.5 mol) of isocyanatoethyl methacrylate at a temperature between room temperature and 30° C. is added dropwise to the flask. The desired reaction product of the abovementioned formula I is precipitated in the reaction mixture in solid form during the dropwise addition. After the reaction is complete the mixture is allowed to react further for about 1 hour, the solid reaction product is subsequently separated from the liquid component by suction filtration, the solid product is washed twice with 30 ml of diethyl ether in each case and dried under vacuum. The yield of the desired compound of the abovementioned formula I is 85.8 g (85.7% of the theoretical yield); melting point: 62°–65° C. The product is soluble in various organic solvents and in styrene and/or acrylates and has little solubility in water. The IR spectrum and the $^1H$ NMR spectrum are consistent with the structure of the urea compound in accordance with the abovementioned formula I.

EXAMPLE 3

Preparation of the Formula I Compound

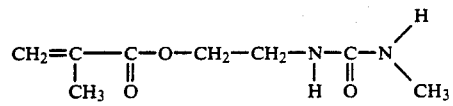

The process is carried out as described in Example 1, but with the difference that instead of ammonia gas at least 1 mol of dry, gaseous methylamine is passed into the reaction mixture. The yield of solid reaction product of the abovementioned formula I is 159.4 g (85.6% of the theoretical yield); melting point: 62°–67° C. The product is readily soluble in water and in various organic solvents. The IR spectrum and the $^1H$ NMR spectrum are consistent with the structure of the urea compound in accordance with the abovementioned formula I.

EXAMPLE 4

Preparation of the Formula I Compound

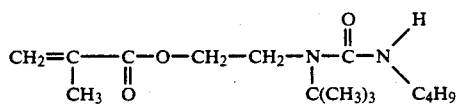

The apparatus described in Example 2 is used and the process described in Example 2 is followed but with the following difference. Instead of n-butylamine, 92.5 g (0.5mol) of tert.-butylaminoethyl methacrylate in toluene with the Sn catalyst are placed in the flask and instead of isocyanatoethyl methacrylate, 49.6 g (0.5 mol) of butyl isocyanate are metered in. The yield of liquid, highly viscous, yellowish reaction product of the abovementioned formula I is 136.2 g (95.9% of the theoretical yield). The product has good miscibility with various organic solvents and is only sparingly miscible with water. The IR spectrum and the $^1H$ NMR spectrum are consistent with the structure of the urea compound in accordance with the abovementioned formula I.

EXAMPLE 5

Preparation of the Formula I Compound

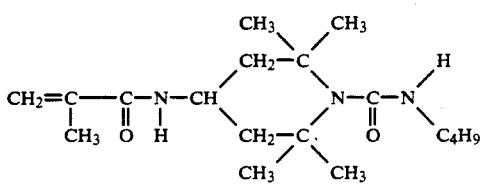

The apparatus described in Example 2 is used and the process described in Example 2 is followed, but with the following difference. Instead of n-butylamine, 48.9 g (0.2 mol) of 4-methacrylamido-2,2,6,6-tetramethylpiperidine (MATMP) in toluene with the Sn catalyst are placed in the flask and instead of isocyanatoethyl methacrylate, 19.8 g (0.2 mol) of n-butyl isocyanate are metered in at 40° C. The yield of solid reaction product of the above-mentioned formula I is 36 g (52.4% of the theoretical yield); melting point: 128° C. The product exhibits only slight solubility both in water and in organic solvents. The IR spectrum and the $^1$H NMR spectrum are consistent with the structure of the urea compound in accordance with the abovementioned formula I.

EXAMPLE 6

Preparation of the Formula I Compound

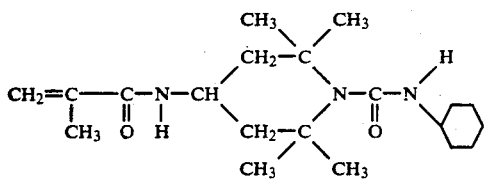

The apparatus described in Example 2 is used and the process described in Example 2 is followed, but with the following difference. Instead of n-butylamine, 122.2 g (0.5 mol) of MATMP (cf. Example 5) in toluene with the Sn catalyst are placed in the flask and instead of isocyanatoethyl methacrylate, 62.5 g (0.5 mol) of cyclohexyl isocyanate at 50° C. are metered in. The yield of solid reaction product of the abovementioned formula I is 103.5 g (56% of the theoretical yield); melting point: 129° C. The product exhibits only slight solubility both in water and in organic solvents. The IR spectrum and the $^1$H NMR spectrum are consistent with the structure of the urea compound in accordance with the abovementioned formula I.

EXAMPLE 7

Preparation of the Formula I Compound

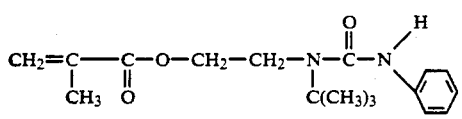

The apparatus described in Example 2 is used and the process as described in Example 2 is followed but with the following difference. Instead of n-butylamine, 92.5 g (0.5 mol) of tert.-butylaminoethyl methacrylate in toluene with the Sn catalyst are placed in the flask and instead of isocyanatoethyl methacrylate, 59.6 g (0.5 mol) of phenyl isocyanate at 50° C. are metered in. The yield of solid reaction product of the abovementioned formula I is 150.6 g (99% of the theoretical yield); melting point: 63° C. The product is slightly soluble in various organic solvents and has little solubility in water. The IR spectrum and the $^1$H NMR spectrum are consistent with the structure of the urea compound in accordance with the abovementioned formula I.

EXAMPLE 8

Preparation of the Formula I Compound

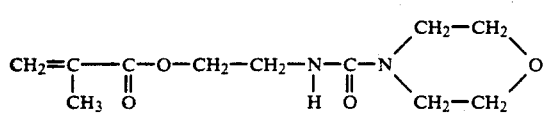

The apparatus described in Example 2 is used and the process as described in Example 23 is followed, but with the following difference. Instead of n-butylamine, 77.5 g (0.5 mol) of isocyanatoethyl methacrylate in toluene with the Sn catalyst are placed in the flask and instead of isocyanatoethyl methacrylate, 43.6 g (0.5 mol) of morpholine at 30° C. are metered in. The yield of solid reaction product of the abovementioned formula I is 116.9 g (96.5% of the theoretical yield); melting point: 132° C. The product exhibits only slight solubility both in water and in organic solvents. The IR spectrum and the $^1$H NMR spectrum are consistent with the structure of the urea compound in accordance with the abovementioned formula I.

EXAMPLE 9

Preparation of the Formula I Compound

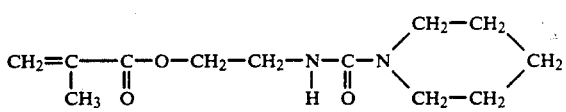

The apparatus described in Example 2 is used and the process as described in Example 2 is followed but with the following difference. Instead of n-butylamine, 77.5 g (0.5 mol) of isocyanatoethyl methacrylate in toluene with the Sn catalyst are placed in the flask and instead of isocyanatoethyl methacrylate, 42.6 g (0.5 mol) of piperidine at 30° C are metered in. The yield of solid reaction product of the abovementioned formula I is 107.0 g (89.1% of the theoretical yield); melting point: 88° C. The product has good solubility in various organic solvents and has little solubility in water. The IR spectrum and the $^1$H NMR spectrum are consistent with the structure of the urea compound in accordance with the abovementioned formula I.

We claim:

1. An ethylenically unsaturated urea derivative of the formula

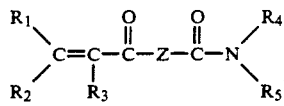

$R_1$, $R_2$ and $R_3$ are individually hydrogen or methyl,

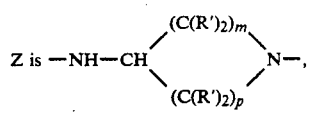

$R^1$ is hydrogen or —CH$_3$, m and p are a number of at least 1 and $m+p=3$ to 5, $R_4$ and $R_5$ are individually selected from the group consisting of hydrogen, alkyl of 1 to 30 carbon atoms,

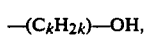

k is 1 to 8, carbocyclic aryl of 6 to 10 carbon atoms, carbocyclic aralkyl of 7 to 30 carbon atoms, cycloalkyl of 5 to 8 carbon atoms or $R_4$ and $R_5$ together with the nitrogen to which they are attached form a heterocycle selected from the group consisting of pyrrolyl, pyrrolidinyl, piperidinyl and morpholino.

2. An urea derivative of claim 1 wherein $R_4$ is hydrogen and $R_5$ is cycloalkyl of 5 to 8 carbon atoms or carbocyclic aryl.

3. An urea derivative of claim 1 wherein

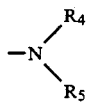

is morpholino.

4. An urea derivative of claim 1 wherein

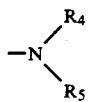

is piperidinyl.

5. An ethylenically unsaturated urea derivative of the formula

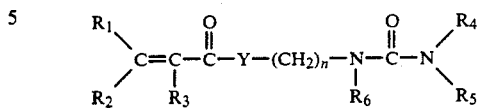

wherein $R_1$, $R_2$ and $R_3$ are individually hydrogen or methyl, Y is —O— or —NH—, n is 2 to 4, $R_6$ is alkyl of 1 to 4 carbon atoms, one of $R_4$ and $R_5$ being hydrogen and the other being a 5 to 7 member heterocycle selected from the group consisting of pyrrolyl, pyrrolidinyl, piperidinyl and morpholino.

* * * * *

UNITED STATES PATENT AND TRADEMARK OFFICE
CERTIFICATE OF CORRECTION

PATENT NO. : 5,079,356

DATED : Jan. 7, 1992

INVENTOR(S) : HANS-ULLRICH HUTH

It is certified that error appears in the above-identified patent and that said Letters Patent is hereby corrected as shown below:

| Col. | Line | |
|---|---|---|
| 8 | 52 | "$R^1$" should be --$R'$-- |

Signed and Sealed this

Thirteenth Day of April, 1993

Attest:

STEPHEN G. KUNIN

Attesting Officer  Acting Commissioner of Patents and Trademarks